United States Patent [19]
Woodriff
[11] Plant 4,073
[45] July 5, 1977

[54] BEGONIA PLANT

[75] Inventor: Leslie Woodriff, McKinleyville, Calif.
[73] Assignee: Mikkelsens Inc., Ashtabula, Ohio

[21] Appl. No.: 691,484
[22] Filed: June 1, 1976
[51] Int. Cl.² ..... A01H 5/00
[52] U.S. Cl. ..... Plt./68
[58] Field of Search ..... Plt./68
*Primary Examiner*—Robert E. Bagwill
*Attorney, Agent, or Firm*—Donald D. Jeffery

EXEMPLARY CLAIM

1. A new and distinct cultivar of begonia plant known by the cultivar name Roulette and particularly characterized as to uniqueness by the combined characteristics of foliage which has an overall ruffled or wavy appearance and which is dark green mottled with yellow-green patches between the veins, and a hairy texture on the margins of the leaves; the leaf petiole often forms a coalesced multi-cylindrical affect at the base of the leaf formed by the fusion of the leaf veins from the two opposite spirals; leaf size of up to 10 cm. wide and up to 8 cm. deep when laid out flat; parted leaf margin with two based lobes that spiral; plant height of upward to 12–15 cm.; very light pink to nearly white flowers, and by its efficient propagation by leaf cuttings.

2 Drawing Figures

The present invention relates to a new and distinctive cultivar or begonia plant, known by the varietal name Roulette and classified as a rhizomatous begonia, produced by me through controlled pollination of two specifically chosen rhizomatous begonia parents in an effort to produce a mottle colored leaf as found in Tiger Kitten, and a spiral leaf base as found in Bowtique. The pollen parent is Tiger Kitten, disclosed in my pending application Ser. No. 610,776, filed Sept. 5, 1975 (now U.S. Plant Pat. No. 3,968), and the seed parent is Bowtique, an unpatented cultivar. Asexual reproduction by stem and leaf cuttings has reproduced the unique features of the new cultivar through successive propagations.

The following characteristics distinguish the new begonia from both its parents and other begonias of this type commercially known and used in the floriculture industry:

1. In comparison to the pollen parent Tiger Kitten, my new cultivar has foliage that has an overall ruffled or wavy appearance.

2. When compared with Tiger Kitten, the new cultivar has darker green foliage mottled with lighter yellow-green patches between the vein. In comparison to the parent cultivar Bowtique, Roulette has better spirals.

3. The new cultivar has greater contrast than Tiger Kitten, with Roulette having a more distinctive hairy texture on the margin of the leaves.

4. The leaf petiole of Tiger Kitten is round and cylindrical to the base of the leaf; the leaf petiole of Roulette often forms a coalesced, multi-cylindrical effect at the base of the leaf formed by a fusion of the leaf veins from the two opposite spirals.

5. Leaf size of Roulette is up to 10 cm. wide by up to 8 cm. deep when laid out flat. The number of leaves produced is approximately 30–40% less than Tiger Kitten.

6. Leaf margin tends to be parted but more properly falls into the begonia classification of spiral type since the two basal lobes do spiral.

7. Plant height is upwards to 12–15 cm.

8. Propagation is most efficient by leaf cuttings but the rhizomes can be divided for reproduction.

The accompanying colored photographs illustrate the overall appearance of the new cultivar taken as a face view of the plant and showing the colors as true as it is reasonably possible to obtain in a colored reproduction of this type. The first sheet of photographic drawings was taken in the spring and shows flowering. The second photograph was taken during the winter and shows the cultivar without flowers.

The following is a detailed description of my new begonia cultivar based on plants produced under commercial practices in McKinleyville, Calif., and Ashtabula, Ohio. Color references are made to the Royal Horticultural Society Colour Chart except where general color terms of ordinary dictionary significance are used.

Parentage: Bowtique × Tiger Kitten (U.S. Plant Pat. No. 3,968).

Propagation: Mostly by using leaf cuttings 4–5 cm. in width having 10–12 mm. of attached leaf petiole remaining for insertion into a media of 50% or more of peat moss with bottom heat 20°–22° C. Roots developed in 18–25 days, and approximately 6 to 8 shoots will emerge in 8–9 weeks after sticking during spring, summer, and fall months.

Rooting habits: Quite rapid for leaf cuttings of this type of begonia; roots are abundant, quite fibrous, and dendritic.

Plant form: Horizontal rhizomatous type with rhizome being partially to fully above ground, forming a bushy type plant.

Habit of growth: Short, compact, very dense, slow to medium rate of growth.

Blooming habits: Small pinkish white flowers are produced annually on racemes having a peduncle up to 30–35 cm. high originating from the rhizome.

Blooming season: Generally in late winter through spring, and often continuous for 4–5 months.

Foliage: Near average in quantity for a rhizomatous type begonia; good texture, firm to hard; excellent keeping qualities.

*Size.*—Mature leaves up to 10 cm. wide by 8 cm. deep, leaf blade wavy, often overlapping.

*Shape.*—Ovate, basal lobes spiral.

*Texture.*—Somewhat luminescent, smooth, glossy, firm.

*Margin.*—Serrate, ciliate.

*Color.*—When grown in heavily shaded environments dark yellow-green 147A with intervenal blotches lighter, yellow-green 146C-D. Color fades to olive green on upper surface and brown red on under surface when grown under high light and high temperature regimes.

lighter, yellow-green 146C-D. Color fades to olive green on upper surface and brown red on under surface when grown under high light and high temperature regimes.

Disease resistance: No foliar diseases have been observed to date; apparently immune to highly resistant to Xanthomanas and powdery mildew when grown with begonias consistently showing infections of these diseases.

FLOWERS:

Borne: On 30–35 cm. long peduncles 2–3 mm. in diameter originating from the rhizome, terminating in a loose raceme. Both the peduncles and the flower pedicels are flecked with short red streaks.

Quantity: Average to above average for a rhizomatous type begonia, total per raceme approximately 30, predominantly male flowers, terminating in pistillated flowers. Buds measure approximately 5 mm. in diameter prior to opening.

Petals: Two opposite, very light pink to nearly white, 10–12 cm. in diameter; total flower diameter 22–25 cm.

Reproductive organs:

*Stamens.*—2–3 mm. in length, light yellow 13-B.

*Pollen.*—Light yellow, fertile.

*Styles/Ovaries.*—Three styles, 5 mm. long and 3 ovaries, 6 mm. wide by 5 mm. deep, white with red flecks, fertile.

I claim:

1. A new and distinct cultivar of begonia plant known by the cultivar name Roulette and particularly characterized as to uniqueness by the combined characteristics of foliage which has an overall ruffled or wavy appearance and which is dark green mottled with yellow-green patches between the veins, and a hairy texture on the margins of the leaves; the leaf petiole often forms a coalesced multi-cylindrical effect at the base of the leaf formed by the fusion of the leaf veins from the two opposite spirals; leaf size of up to 10 cm. wide and up to 8 cm. deep when laid out flat; parted leaf margin with two based lobes that spiral; plant height of upward to 12–15 cm.; very light pink to nearly white flowers, and by its efficient propagation by leaf cuttings.

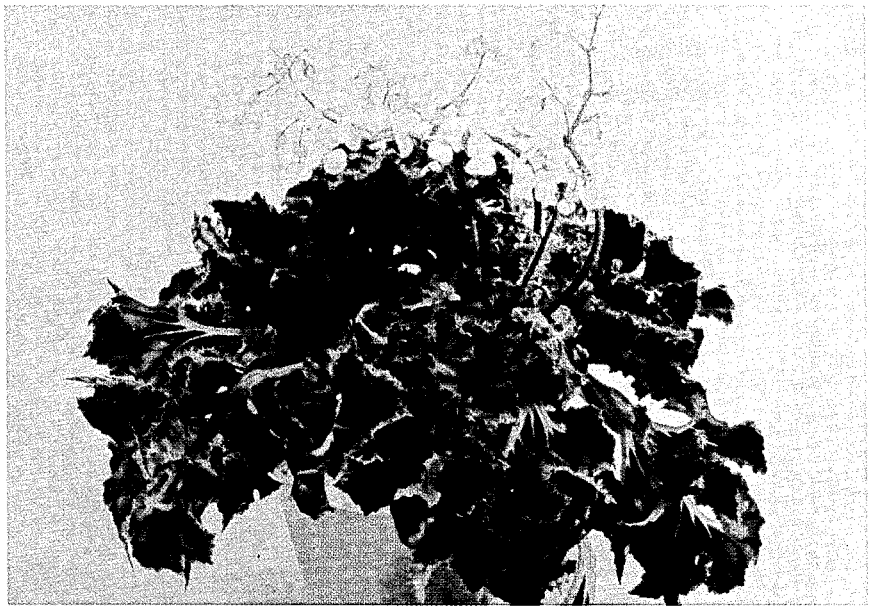

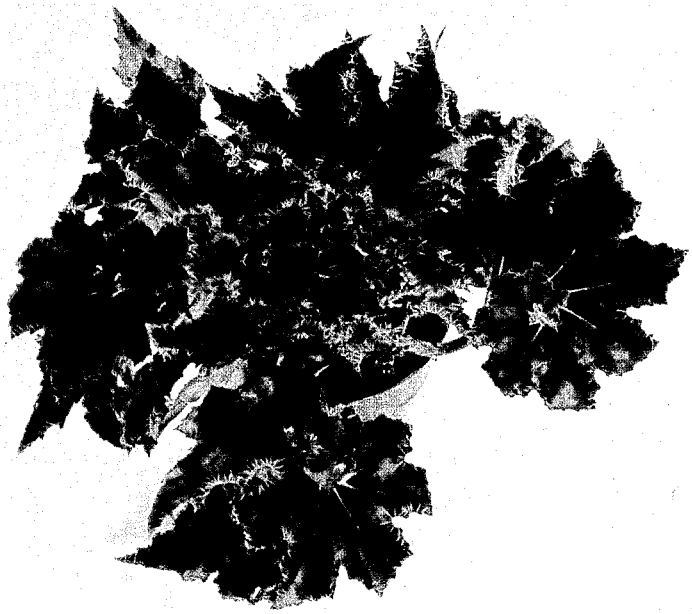

* * * * *